US008914112B2

(12) United States Patent
Whitehurst et al.

(10) Patent No.: US 8,914,112 B2
(45) Date of Patent: Dec. 16, 2014

(54) METHODS AND SYSTEMS OF TREATING PANCREATITIS PAIN CAUSED BY SPHINCTER OF ODDI DYSFUNCTION

(75) Inventors: Todd K. Whitehurst, Santa Clarita, CA (US); Rafael Carbunaru, Valley Village, CA (US); Kristen N. Jaax, Santa Clarita, CA (US); Andrew DiGiore, Santa Monica, CA (US); Brett Schleicher, Valencia, CA (US); Greg Baldwin, Valencia, CA (US); Roger Hastings, Maple Grove, MN (US)

(73) Assignee: Boston Scienctific Neuromodulation Corporation, Valencia, CA (US)

(*) Notice: Subject to any disclaimer, the term of this patent is extended or adjusted under 35 U.S.C. 154(b) by 1408 days.

(21) Appl. No.: 12/358,002

(22) Filed: Jan. 22, 2009

(65) Prior Publication Data

US 2009/0192557 A1 Jul. 30, 2009

Related U.S. Application Data

(60) Provisional application No. 61/022,987, filed on Jan. 23, 2008.

(51) Int. Cl.
*A61N 1/36* (2006.01)
*A61N 1/372* (2006.01)

(52) U.S. Cl.
CPC ........ *A61N 1/36007* (2013.01); *A61N 1/36071* (2013.01); *A61N 1/37205* (2013.01); *A61N 1/37252* (2013.01)
USPC .............................................. 607/40; 607/46

(58) Field of Classification Search
USPC .................................................. 607/40, 46, 3
See application file for complete search history.

(56) References Cited

U.S. PATENT DOCUMENTS

| 5,147,294 | A | 9/1992 | Smith et al. |
| 5,193,539 | A | 3/1993 | Schulman et al. |
| 5,193,540 | A | 3/1993 | Schulman et al. |
| 5,312,439 | A | 5/1994 | Loeb |
| 5,501,703 | A | 3/1996 | Holsheimer et al. |
| 5,938,688 | A | 8/1999 | Schiff |
| 6,016,449 | A | 1/2000 | Fischell et al. |
| 6,051,017 | A | 4/2000 | Loeb et al. |
| 6,164,284 | A | 12/2000 | Schulman et al. |
| 6,185,452 | B1 | 2/2001 | Schulman et al. |
| 6,208,094 | B1 | 3/2001 | Morrish |
| 6,208,894 | B1 | 3/2001 | Schulman et al. |
| 6,280,873 | B1 | 8/2001 | Tsukamoto |
| 6,381,496 | B1 | 4/2002 | Meadows et al. |

(Continued)

FOREIGN PATENT DOCUMENTS

| WO | WO 02087653 | 11/2002 |
| WO | WO 2006116165 | 11/2006 |
| WO | WO 2007038200 | 4/2007 |
| WO | WO 2007109656 | 9/2007 |

*Primary Examiner* — Alyssa M Alter
(74) *Attorney, Agent, or Firm* — Vista IP Law Group LLP

(57) ABSTRACT

Methods and systems of treating a patient with pancreatitis pain include providing a stimulator, configuring one or more stimulation parameters to control sphincter of Oddi function, programming the stimulator with the one or more stimulation parameters, generating a stimulus configured to control sphincter of Oddi function with the stimulator in accordance with the one or more stimulation parameters, and applying the stimulus with the stimulator to one or more stimulation sites in accordance with the one or more stimulation parameters.

14 Claims, 13 Drawing Sheets

(56) References Cited

U.S. PATENT DOCUMENTS

| | | |
|---|---|---|
| 6,458,171 B1 | 10/2002 | Tsukamoto |
| 6,487,446 B1 | 11/2002 | Hill et al. |
| 6,516,227 B1 | 2/2003 | Meadows et al. |
| 6,539,263 B1 | 3/2003 | Schiff et al. |
| 6,553,263 B1 | 4/2003 | Meadows et al. |
| 6,591,137 B1 * | 7/2003 | Fischell et al. ............... 607/40 |
| 6,596,439 B1 | 7/2003 | Tsukamoto et al. |
| 6,605,383 B1 | 8/2003 | Wu |
| 6,607,843 B2 | 8/2003 | Ruth, II et al. |
| 6,760,626 B1 | 7/2004 | Boveja |
| 6,761,715 B2 | 7/2004 | Carroll |
| 7,193,539 B2 | 3/2007 | Kim et al. |
| 7,458,968 B2 | 12/2008 | Carroll |
| 7,501,703 B2 | 3/2009 | Minervini |
| 2007/0049793 A1 | 3/2007 | Ignagni et al. |
| 2007/0073354 A1 | 3/2007 | Knudson et al. |
| 2007/0106338 A1 * | 5/2007 | Errico ............................ 607/42 |
| 2007/0225781 A1 | 9/2007 | Saadat et al. |
| 2008/0154333 A1 | 6/2008 | Knudson et al. |

\* cited by examiner

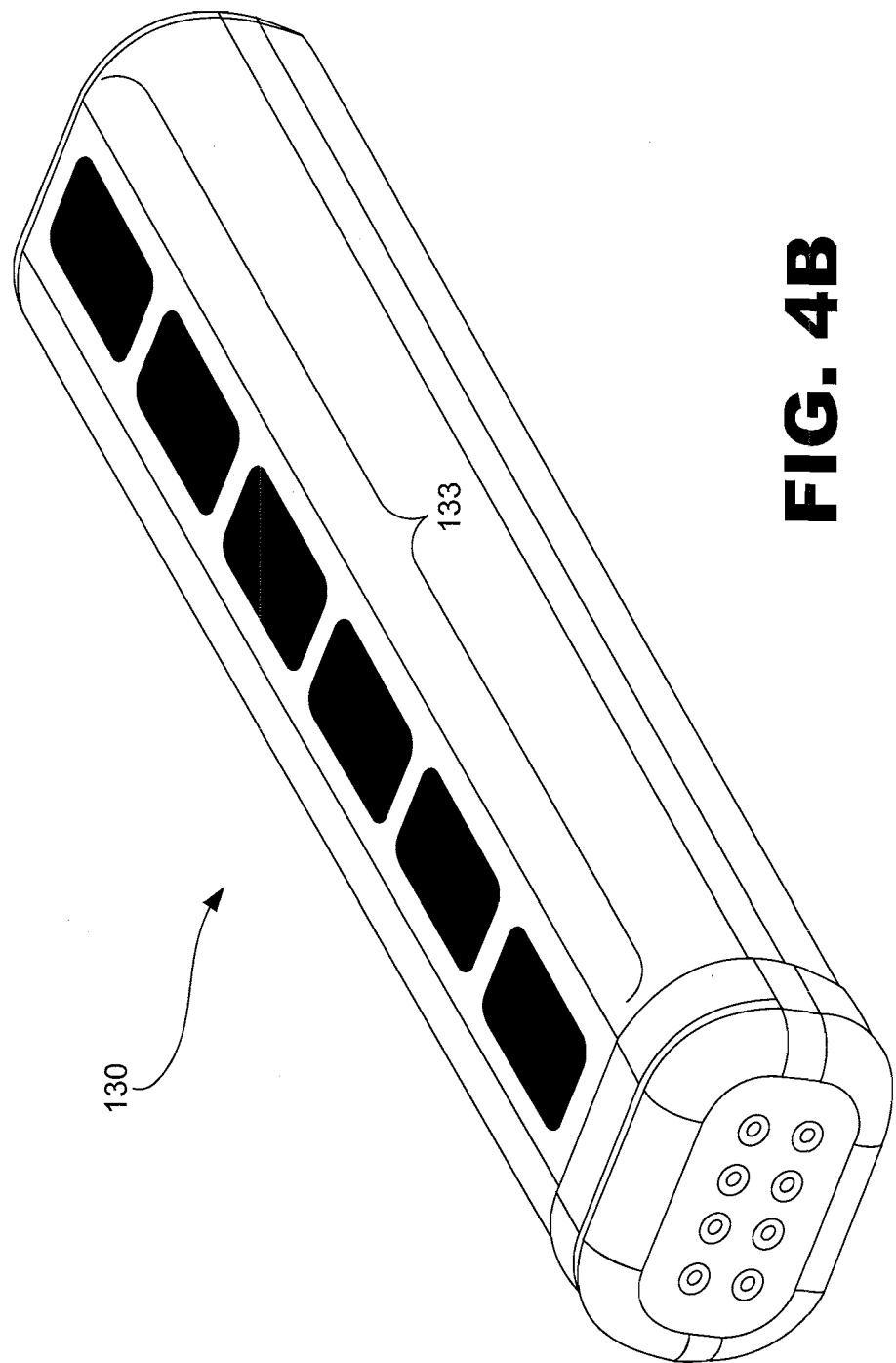

METHODS AND SYSTEMS OF TREATING PANCREATITIS PAIN CAUSED BY SPHINCTER OF ODDI DYSFUNCTION

RELATED APPLICATIONS

The present application claims priority under 35 U.S.C. §119(e) to U.S. Provisional Patent Application No. 61/022,987 by Todd K. Whitehurst et al., filed on Jan. 23, 2008, and entitled "METHODS AND SYSTEMS OF TREATING PANCREATITIS PAIN CAUSED BY SPHINCTER OF ODDI DYSFUNCTION," the contents of which are hereby incorporated by reference in their entirety.

BACKGROUND

The pancreas is a gland located deep in the abdomen between the stomach and the spine. The pancreas performs exocrine and endocrine functions. Its exocrine functions include secreting pancreatic juice containing digestive enzymes into the digestive tract. Its endocrine functions include producing hormones such as insulin glucagon, and somatostatin, for controlled release into the bloodstream.

The sphincter of Oddi is a muscular structure that encompasses the confluence of the distal common bile duct and the pancreatic duct of the pancreas as they penetrate the wall of the duodenum. The term "sphincter of Oddi dysfunction" describes a clinical syndrome of biliary or pancreatic obstruction related to mechanical or functional abnormalities of the sphincter of Oddi. The sphincter of Oddi is composed of small circular and longitudinal muscular segments that are approximately six to ten millimeters in total length and are contained mostly within the wall of the duodenum. The muscle fibers surround the intraduodenal segment of the common bile duct and the ampulla of Vater.

Sphincter of Oddi dysfunction has been hypothesized as a cause of idiopathic recurrent pancreatitis and pancreatitis occurring after endoscopic retrograde cholangiopancreatography (ERCP). To illustrate, sphincter of Oddi dysfunction may lead to a build-up of pancreatic juices within the pancreatic and bile ducts, thereby causing ductal distension, tissue damage, and pain. Due to the increased pressure in the duct, the fluid may seek alternate, unnatural routes for release, which may lead to the development of fissures in the pancreas. These fissures may leak pancreatic enzymes that digest surrounding tissues and organs and thereby cause severe abdominal pain and organ damage.

SUMMARY

Methods of treating a patient with pancreatitis pain include providing a stimulator, configuring one or more stimulation parameters to control sphincter of Oddi function, programming the stimulator with the one or more stimulation parameters, generating a stimulus configured to control sphincter of Oddi function with the stimulator in accordance with the one or more stimulation parameters, and applying the stimulus with the stimulator to one or more stimulation sites in accordance with the one or more stimulation parameters.

Systems for treating a patient with pancreatitis pain include a stimulator configured to generate at least one stimulus in accordance with one or more stimulation parameters adjusted to control sphincter of Oddi function, a programmable memory unit in communication with the stimulator and programmed to store the one or more stimulation parameters to at least partially define the stimulus such that the stimulus is configured to control sphincter of Oddi function, and means, operably connected to the stimulator, for applying the stimulus to one or more stimulation sites.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIG. 4B shows an example of a microstimulator with a plurality of electrodes disposed on an outer surface thereof according to principles described herein.

Throughout the drawings, identical reference numbers designate similar, but not necessarily identical, elements.

DETAILED DESCRIPTION

Methods and systems for treating a patient with pancreatitis pain caused by sphincter of Oddi dysfunction are described herein. As used herein, "pancreatitis pain" refers to any type of pain caused by other otherwise associated with pancreatitis resulting from sphincter of Oddi dysfunction.

In some examples, electrical stimulation may be applied to a suitable stimulation site within a patient to control the contraction and relaxation of the sphincter of Oddi. Exemplary stimulation sites may include efferent nerves that innervate the sphincter of Oddi, including the pre-ganglionic cholinergic nerves. The stimulator may be configured to apply at least one stimulus to one or more such stimulation sites in accordance with one or more stimulation parameters. The stimulus may be used to regulate the function of the sphincter of Oddi and, for example, release pancreatic build-up and reduce ductal hypertension, thereby decreasing the pain associated with pancreatitis and sphincter of Oddi dysfunction.

A number of advantages are associated with the systems and methods described herein. For example, the techniques used to implant the stimulator may be minimally invasive and carry a low risk of external scarring. The procedures described herein for treating pancreatitis pain may be reversible in that implanted devices may be turned off and/or removed at any time. Moreover, adjustments to the stimulation parameters may be made throughout the treatment period by reprogramming the implanted stimulator via, for example, a transcutaneous communication link.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

To facilitate an understanding of the systems and methods described herein, a brief overview of the etymology of sphincter of Oddi dysfunction and pancreatitis pain will be given in connection with FIGS. 1A and 1B.

Figure 1A:
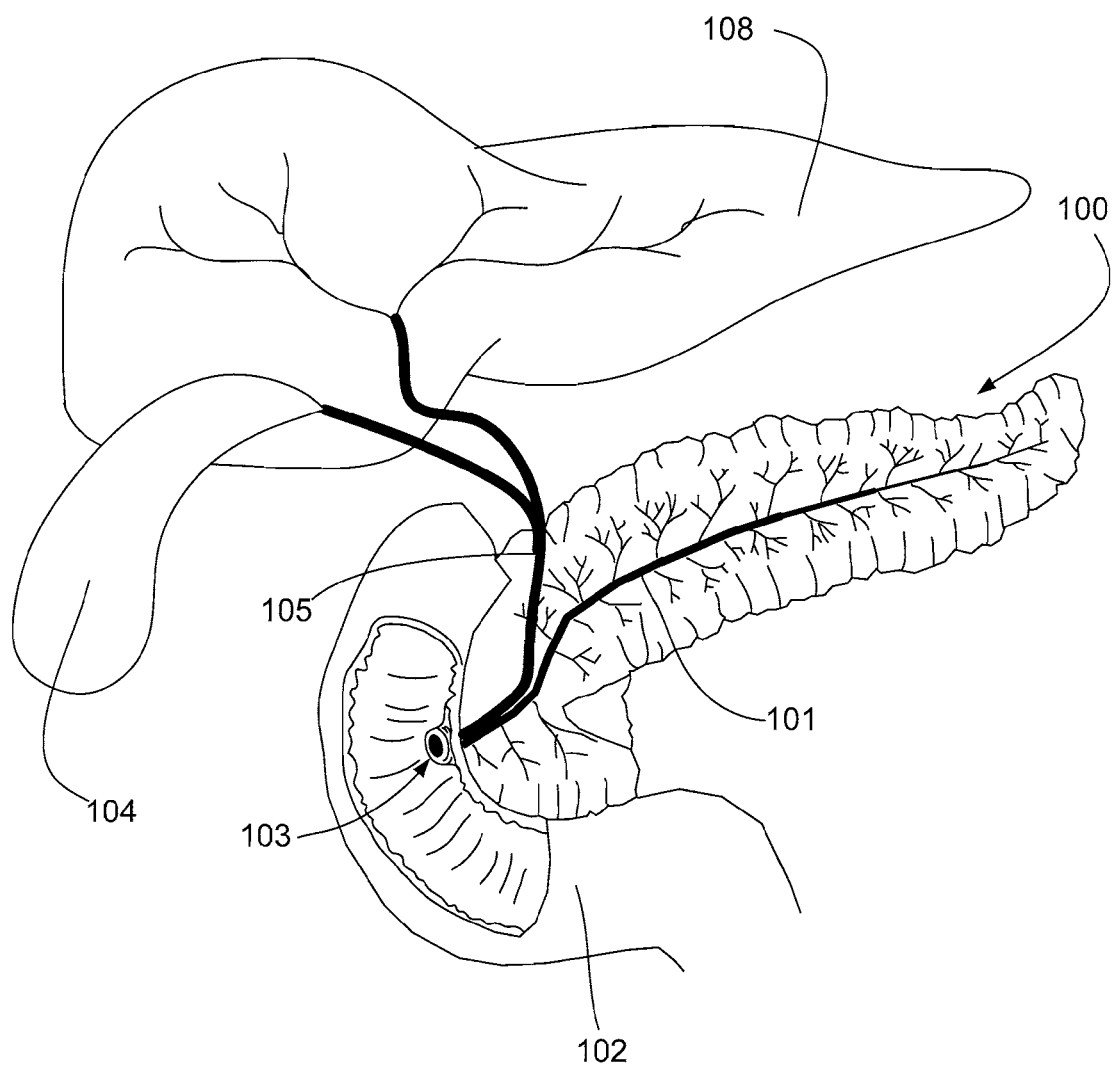
FIG. 1A is a front view of an exemplary human pancreas, liver, gallbladder and a portion of the duodenum including the sphincter of Oddi.

FIG. 1A is a front view of a human pancreas 100, duodenum 102, liver 108, and gall bladder 104. As shown in FIG. 1A, the pancreas 100 is in direct contact with the duodenum 102, which is the first part of the small intestine and responsible for the breakdown of food within the small intestine. The pancreas 100 includes both endocrine and exocrine tissue. Endocrine tissue produces and secretes hormones such as insulin, glucagon, somatostatin, and others into the bloodstream level. Exocrine tissue produces and secretes into the duodenum 102 pancreatic juice containing enzymes (e.g., trypsin, chymotrypsin, and bicarbonate ions) that break down digestible foods within the digestive tract. This secretion is controlled by a group of muscle fibers called the sphincter of Oddi 103. As will be described in more detail below, pancreatitis and associated pancreatitis pain are often caused by dysfunction of the sphincter of Oddi 103.

The motility of the sphincter of Oddi 103 is complex and varies during fasting and fed states. During the fasting state, sphincter of Oddi motility is integrated with waves of activity that sweep through the intestines in a regular cycle (also known as a migrating motor complex), thus permitting coordinated release of bile into the duodenum 102. Myoelectrical potentials within the sphincter of Oddi 103 increase during the three phases of the migrating motor complex, and then decrease rapidly. During the fed state, myoelectrical potentials within the sphincter of Oddi vary depending upon the type and quantity of nutrients ingested and may also be influenced by certain endogenous hormones such as cholecystokinin.

The exocrine tissue of the pancreas 100 includes a large number of ducts arranged in clusters referred to as acini. Pancreatic juices are first secreted into a lumen of each acinus. The juices accumulate within these ducts and eventually drain into a main duct known as the pancreatic duct 101. The pancreatic duct 101 is joined near the sphincter of Oddi by the common bile duct 105, which is the duct that carries bile from the liver and the gall bladder. These two ducts empty directly into the duodenum 102 through the sphincter of Oddi 103. The sphincter of Oddi 103 contracts and dilates to regulate the flow of bile and pancreatic juice into the duodenum 102.

Pancreatitis is a painful condition in which the pancreas 100 becomes inflamed. Pancreatitis may be chronic or acute. As mentioned, one cause of pancreatitis may be the dysfunction of the sphincter of Oddi 103 which hinders the flow of pancreatic juices through the pancreatic duct 101. To illustrate, the sphincter of Oddi 103 may remain in a contracted state and not allow adequate drainage of the pancreatic and bile ducts. This hindrance of the natural passage of pancreatic juices into the gastrointestinal tract may cause the pancreatic juices to build up within the pancreas 100, thus creating ductal distension, tissue damage, and pain. Due to the increased pressure in the pancreatic duct 101 and other ducts, pancreatic juices may seek alternate and unnatural routes for release which may consequentially lead to the development of fissures in the pancreas 100. These fissures may leak pancreatic enzymes that digest surrounding tissues and organs, leading to severe abdominal pain and organ damage.

Figure 1B:
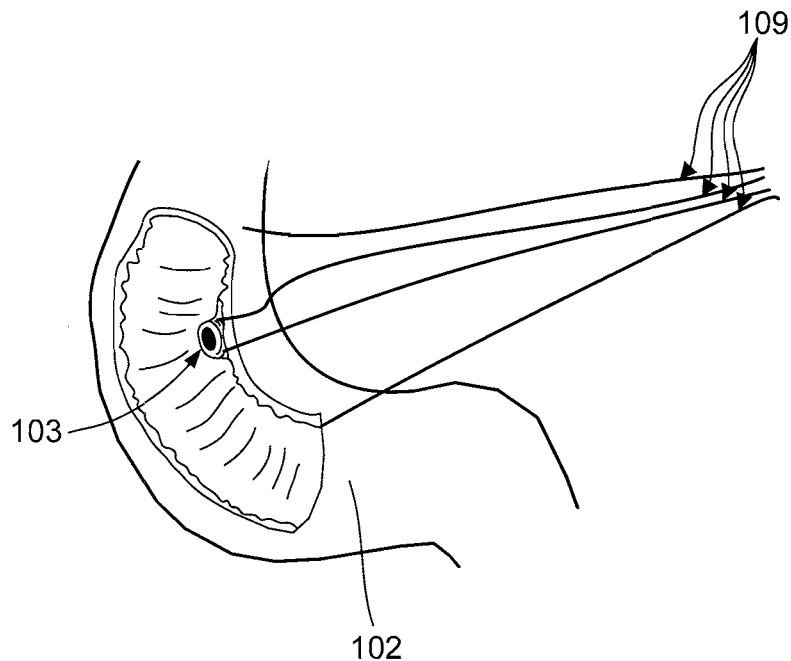
FIG. 1B illustrates a number of nerves that innervate the sphincter of Oddi.

FIG. 1B is a front view of the sphincter of Oddi 103 showing a partial innervation thereof. The sphincter of Oddi 103 is innervated by pre-ganglionic cholinergic nerves 109. The sphincter of Oddi 103 may be contracted through stimulation of one or more of these nerves 109.

It is believed that applying a stimulus to one or more stimulation sites within a patient may be useful in controlling the function of the sphincter of Oddi. Pancreatitis caused by sphincter of Oddi dysfunction and pain associated therewith may consequently be alleviated. As used herein, the term "stimulation site" may refer to one or more regions of the sphincter of Oddi and/or one or more nerves that innervate the sphincter of Oddi. For example, the stimulation site may include, but is not limited to one or more of the sympathetic or parasympathetic nerves innervating the sphincter of Oddi, one ore more of the pre-ganglionic cholinergic nerves innervating the sphincter of Oddi, one or more efferent nerves innervating the sphincter of Oddi, and/or any tissue of, or near, the sphincter of Oddi.

In some examples, the stimulus may be configured to block or evoke the myoelectrical potentials in the muscles of the sphincter of Oddi, thereby inducing contraction and/or relaxation of the sphincter of Oddi. By regulating the function of the sphincter of Oddi, pancreatic build-up can be released and ductal hypertension may be reduced. In this manner, pancreatic function may be improved and pancreatitis pain may be decreased.

Consequently, a stimulator may be implanted within a patient to deliver a stimulus to one or more of the stimulation sites described herein to treat pancreatitis pain caused by sphincter of Oddi dysfunction. The stimulus may include an electrical stimulation current and/or the infusion of one or more therapeutic drugs at the stimulation site.

As used herein, and in the appended claims, the term "stimulator" will be used broadly to refer to any device that delivers a stimulus to a stimulation site to treat pancreatitis pain. Thus, the term "stimulator" includes, but is not limited to, a microstimulator, implantable pulse generator (IPG), spinal cord stimulator (SCS), external trial stimulator, system control unit, deep brain stimulator, drug pump, stent electrode, or similar devices.

Figure 2:
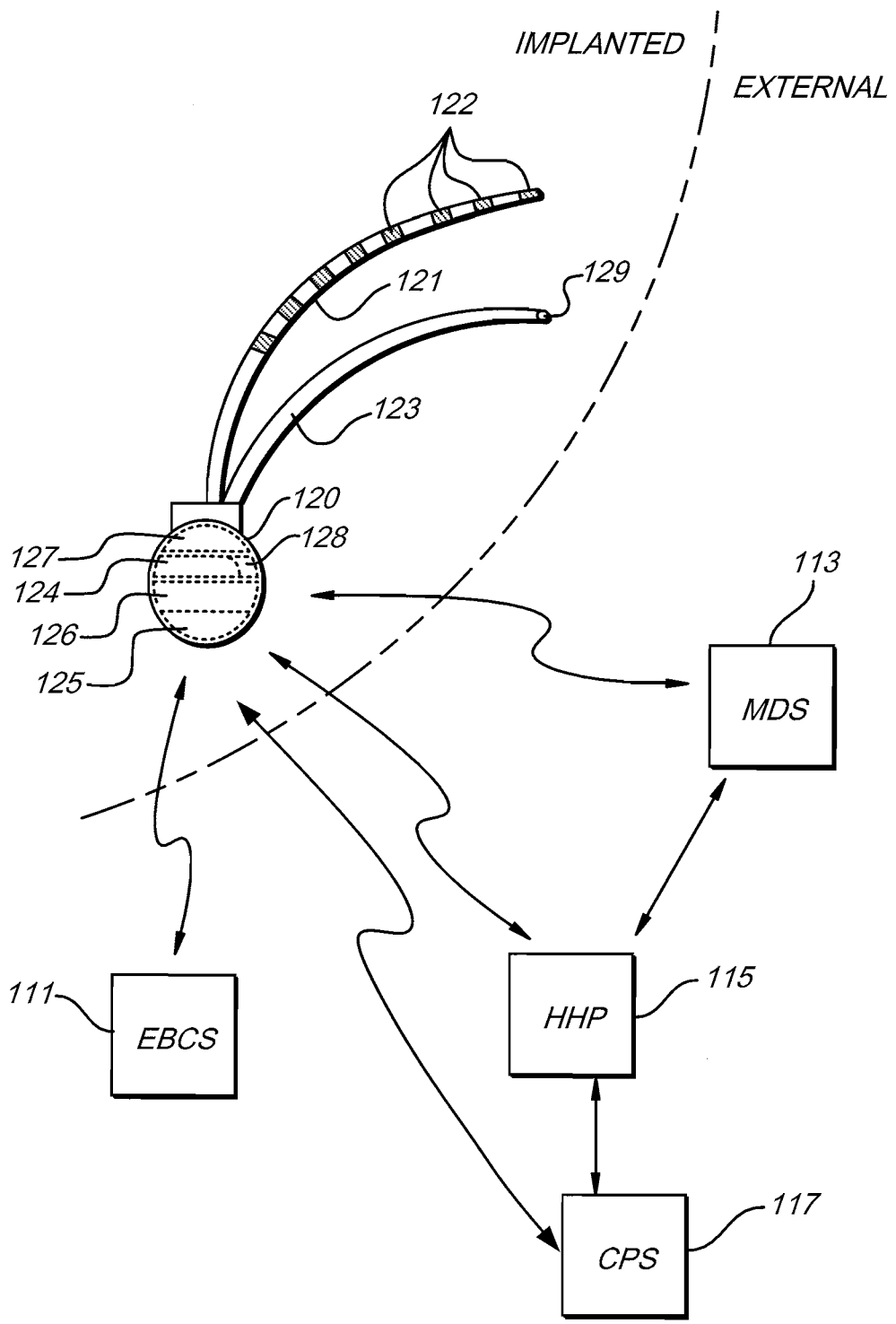
FIG. 2 illustrates an exemplary implantable stimulator according to principles described herein.

A more detailed description of an exemplary stimulator and its operation will now be given in connection with FIG. 2. FIG. 2 illustrates an exemplary stimulator 120 that may be used to apply a stimulus to a stimulation site within a patient, e.g., an electrical stimulation of the stimulation site, an infusion of one or more drugs at the stimulation site, or both. The electrical stimulation function of the stimulator 120 will be described first, followed by an explanation of the possible drug delivery function of the stimulator 120. It will be understood, however, that the stimulator 120 may be configured to provide only electrical stimulation, only drug stimulation, both types of stimulation, or any other type of stimulation as best suits a particular patient.

The exemplary stimulator 120 shown in FIG. 2 is configured to provide electrical stimulation to one or more stimulation sites within a patient and may include at least one lead 121 coupled thereto. In some examples, the at least one lead 121 includes a number of electrodes 122 through which electrical stimulation current may be applied to a stimulation site. It will be recognized that the at least one lead 121 may include any number of electrodes 122 arranged in any configuration as best serves a particular application. In some alternative examples, as will be described in more detail below, the stimulator 120 may be leadless.

As illustrated in FIG. 2, the stimulator 120 includes a number of components. It will be recognized that the stimulator 120 may include additional and/or alternative components as best serves a particular application. A power source 125 is configured to output voltage used to supply the various components within the stimulator 120 with power and/or to generate the power used for electrical stimulation. The power source 125 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like.

In some examples, the power source 125 may be recharged using an external charging system. One type of rechargeable power supply that may be used is described in U.S. Pat. No. 6,596,439, which is incorporated herein by reference in its entirety. Other battery construction techniques that may be used to make the power source 125 include those shown, e.g., in U.S. Pat. Nos. 6,280,873; 6,458,171; 6,605,383; and 6,607,843, all of which are incorporated herein by reference in their respective entireties.

The stimulator 120 may also include a coil 128 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 125.

For example, an external battery charging system (EBCS) 111 may be provided to generate power that is used to recharge the power source 125 via any suitable communication link. Additional external devices including, but not limited to, a hand held programmer (HHP) 115, a clinician programming system (CPS) 117, and/or a manufacturing and diagnostic system (MDS) 113 may also be provided and configured to activate, deactivate, program, and/or test the stimulator 120 via one or more communication links. It will be recognized that the communication links shown in FIG. 2 may each include any type of link used to transmit data or energy, such as, but not limited to, an RF link, an infrared (IR) link, an optical link, a thermal link, or any other energy-coupling link.

Additionally, if multiple external devices are used in the treatment of a patient, there may be communication among those external devices, as well as with the implanted stimulator 120. It will be recognized that any suitable communication link may be used among the various devices illustrated.

The external devices shown in FIG. 2 are merely illustrative of the many different external devices that may be used in connection with the stimulator 120. Furthermore, it will be recognized that the functions performed by any two or more of the external devices shown in FIG. 2 may be performed by a single external device.

The stimulator 120 may also include electrical circuitry 124 configured to generate the electrical stimulation current that is delivered to a stimulation site via one or more of the electrodes 122. For example, the electrical circuitry 124 may include one or more processors, capacitors, integrated circuits, resistors, coils, and/or any other component configured to generate electrical stimulation current.

Additionally, the exemplary stimulator 120 shown in FIG. 2 may be configured to provide drug stimulation to a patient by applying one or more drugs at a stimulation site within the patient. To this end, a pump 127 may also be included within the stimulator 120. The pump 127 may be configured to store and dispense one or more drugs, for example, through a catheter 123. The catheter 123 may be coupled at a proximal end to the stimulator 120 and may have an infusion outlet 129 for infusing dosages of the one or more drugs at the stimulation site. In some embodiments, the stimulator 120 may include multiple catheters 123 and/or pumps for storing and infusing dosages of the one or more drugs at the stimulation site.

In some examples, the one or more drugs may have an excitatory or inhibitory effect on the stimulation site. In this manner, one or more drugs may be applied to the stimulation site to assist in inducing contraction and/or relaxation of the sphincter of Oddi.

Exemplary drugs that may be applied to a stimulation site to treat pancreatitis pain by controlling sphincter of Oddi function include, but are not limited to, at least one or more of the following: an excitatory neurotransmitter (e.g., glutamate, dopamine, norepinephrine, epinephrine, acetylcholine, serotonin); an excitatory neurotransmitter agonist (e.g., glutamate receptor agonist, L-aspartic acid, N-methyl-D-aspartic acid (NMDA), bethanechol, norepinephrine); an inhibitory neurotransmitter antagonist(s) (e.g., bicuculline); an agent that increases the level of an excitatory neurotransmitter (e.g., edrophonium, Mestinon); and/or an agent that decreases the level of an inhibitory neurotransmitter (e.g., bicuculline).

Exemplary inhibitory drugs that may be applied to a stimulation site to treat pancreatitis pain by controlling sphincter of Oddi function include, but are not limited to, at least one or more of the following: an inhibitory neurotransmitter(s) (e.g., gamma-aminobutyric acid, a.k.a. GABA, dopamine, glycine); an agonist of an inhibitory neurotransmitter (e.g., a GABA receptor agonist such as midazolam or clondine, muscimol); an excitatory neurotransmitter antagonist(s) (e.g. prazosin, metoprolol, atropine, benztropine); an agent that increases the level of an inhibitory neurotransmitter; an agent that decreases the level of an excitatory neurotransmitter (e.g., acetylcholinesterase, Group II metabotropic glutamate receptor (mGluR) agonists such as DCG-IV); a local anesthetic agent (e.g., lidocaine); and/or an analgesic medication. It will be understood that some of these drugs, such as dopamine, may act as excitatory neurotransmitters in some stimulation sites and circumstances, and as inhibitory neurotransmitters in other stimulation sites and circumstances.

Additional or alternative drugs that may be applied to a stimulation site to treat pancreatitis pain include, but are not limited to, steroids, antibiotics, anticonvulsants, antidepressants, and gangliosides. These compounds have been shown to increase efficacy of drug infusion, reduce fibrosis, and/or prevent infection.

Any of the drugs listed above, alone or in combination, or other drugs or combinations of drugs developed or shown to treat pancreatitis pain by controlling sphincter of Oddi function may be applied to the stimulation site. In some embodiments, the one or more drugs are infused chronically into the stimulation site. Additionally or alternatively, the one or more drugs may be infused acutely into the stimulation site in response to a biological signal or a sensed need for the one or more drugs.

The stimulator 120 may also include a programmable memory unit 126 configured to store one or more stimulation parameters. The stimulation parameters may include, but are not limited to, electrical stimulation parameters, drug stimulation parameters, and other types of stimulation parameters. The programmable memory unit 126 allows a patient, clinician, or other user of the stimulator 120 to adjust the stimulation parameters such that the stimulation applied by the stimulator 120 is safe and efficacious for treatment of a particular patient. The programmable memory unit 126 may include any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., continuous or intermittent), duty cycle or burst repeat interval, ramp on time, and ramp off time. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, continuous, or bolus.

Specific stimulation parameters may have different effects on different types, causes, or symptoms of pancreatitis pain. Thus, in some examples, the stimulation parameters may be adjusted at any time throughout the treatment course as best serves the particular patient being treated. It will be recognized that any of the characteristics of the stimulation current, including, but not limited to, the pulse shape, amplitude, pulse width, frequency, burst pattern (e.g., continuous or intermittent), duty cycle or burst repeat interval, ramp on time, and ramp off time may be adjusted throughout the course of treatment as best serves a particular application.

To illustrate, a baseline set of stimulation parameters may initially be set to begin treatment of pancreatitis pain. These baseline values may be adjusted throughout the course of treatment in response to patient feedback or sensed indicators of sphincter of Oddi dysfunction. Additionally or alternatively, the patient and/or clinician may adjust the stimulation parameters at any time to prevent accommodation, collateral stimulation, and/or ineffectiveness.

In some embodiments, the stimulation parameters may be configured to provide monopolar electrical stimulation. For example, an external case of the stimulator 120 may be used as an indifferent electrode. In other embodiments, the stimulation parameters may be configured to provide bipolar electrical stimulation (e.g., one of the electrodes 122 may be used as an indifferent electrode). Different stimulation parameters may have different effects on neural or other tissue. Therefore, parameters may be chosen to target specific neural or other tissue populations and/or exclude others in order to achieve a desired therapeutic effect. Additionally, the stimulation parameters may provide for current steering between electrodes 122 such that specific stimulation sites may be targeted.

An exemplary baseline set of stimulation parameters that may be used to initially define stimulation current that is used to treat pancreatitis pain by controlling sphincter of Oddi function includes, but is not limited to, the stimulation parameters shown in Table 1. It will be recognized that the baseline set of stimulation parameters shown in Table 1 may vary depending on the particular patient being treated and that additional or alternative stimulation parameters may be defined.

TABLE 1

| Exemplary Baseline Stimulation Parameters | |
|---|---|
| Pulse width | 0.01 microseconds (μsec)-5 milliseconds (msec) |
| Frequency | Greater than 100 Hertz (Hz) to relax a sphincter of Oddi muscle or less than or equal to 100 Hz to contract an sphincter muscle |
| Amplitude | 0.01-15 milliamps (mA) |

Hence, as shown in Table 1, a stimulation current having a pulse width of 0.01 μsec-5 msec and an amplitude of 0.01-15 mA may be initially applied to one or more of sphincter of Oddi muscles and/or one of the parasympathetic and/or sympathetic nerves that innervate the sphincter of Oddi in order to control sphincter of Oddi dysfunction. Any of the stimulation parameters (e.g., the pulse width, burst pattern, frequency, and/or amplitude) may be configured to avoid muscle spasms, nerve damage, and/or discomfort.

As shown in Table 1, the frequency of the stimulation current depends on whether it is desirable to relax or contract the target sphincter of Oddi muscle. In some examples, to induce relaxation of sphincter of Oddi muscles, a stimulation frequency having a frequency greater than 100 Hz may be used. To induce contraction of sphincter of Oddi muscles, a frequency less than or equal to 100 Hz may be used. It will be recognized that the frequency values listed herein are merely exemplary and that they may be adjusted as best serves a particular patient. In some examples, excitation of the parasympathetic nerves innervating the sphincter of Oddi may open the sphincter of Oddi; thus, releasing pancreatic juices or build-up. Excitation of the sympathetic nerves innervating the sphincter of Oddi may close the sphincter of Oddi, preventing unwanted leakage of pancreatic juices into the duodenum.

In some examples, these baseline parameters may be determined in the initial fitting session and may depend on the electrode placement (e.g., how proximal they are to the stimulation site), local impedance (which may be affected by scar tissue, etc.), and patient variability. The clinician or other programmer may make subtle, iterative adjustments to any of the stimulation parameters in response to feedback from the patient.

After a predetermined length of time (e.g., a week, a month, or multiple months) of treatment or as the need may arise, the patient may be evaluated to determine whether the stimulation parameters need to be adjusted and/or whether the additional stimulation is needed in order to treat the pancreatitis pain. In some examples, if the patient no longer exhibits any symptoms of pancreatitis pain, the stimulation may be terminated. Alternatively, if it is determined that the patient needs further treatment, the stimulation may continue in accordance with the same set of stimulation parameters or in accordance with a newly defined set of stimulation parameters. For example, the stimulation parameters may be adjusted from the exemplary baseline stimulation parameters described previously in connection with Table 1 to have values that better suit the needs of the patient and more effectively treat pancreatitis pain by controlling sphincter of Oddi function.

In some examples, the stimulator 120 may be configured to alternatingly cause the sphincter of Oddi to contract and relax. For example, increased pancreatic enzyme production during heightened levels of gastrointestinal activity tends to exacerbate pancreatitis pain caused by sphincter of Oddi dysfunction in some patients. To this end, the stimulation parameters of the stimulator 120 may be configured to simulate normal sphincter of Oddi function by contracting the sphincter of Oddi during periods where gastrointestinal activity is relatively low (e.g., between meals) and relaxing the sphincter of Oddi during periods of relatively higher gastrointestinal activity (e.g., during or right after meals).

The stimulator 120 of FIG. 2 is illustrative of many types of stimulators that may be used in accordance with the systems and methods described herein. For example, the stimulator 120 may include an implantable pulse generator (IPG), a spinal cord stimulator (SCS), a deep brain stimulator, a drug pump, or any other type of implantable device configured to deliver a stimulus to a stimulation site within a patient. Exemplary IPGs suitable for use as described herein include, but are not limited to, those disclosed in U.S. Pat. Nos. 6,381,496; 6,553,263; and 6,760,626. Exemplary spinal cord stimulators suitable for use as described herein include, but are not limited to, those disclosed in U.S. Pat. Nos. 5,501,703; 6,487,446; and 6,516,227. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

The stimulator 120 of FIG. 2 may alternatively include a microstimulator. Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 3:
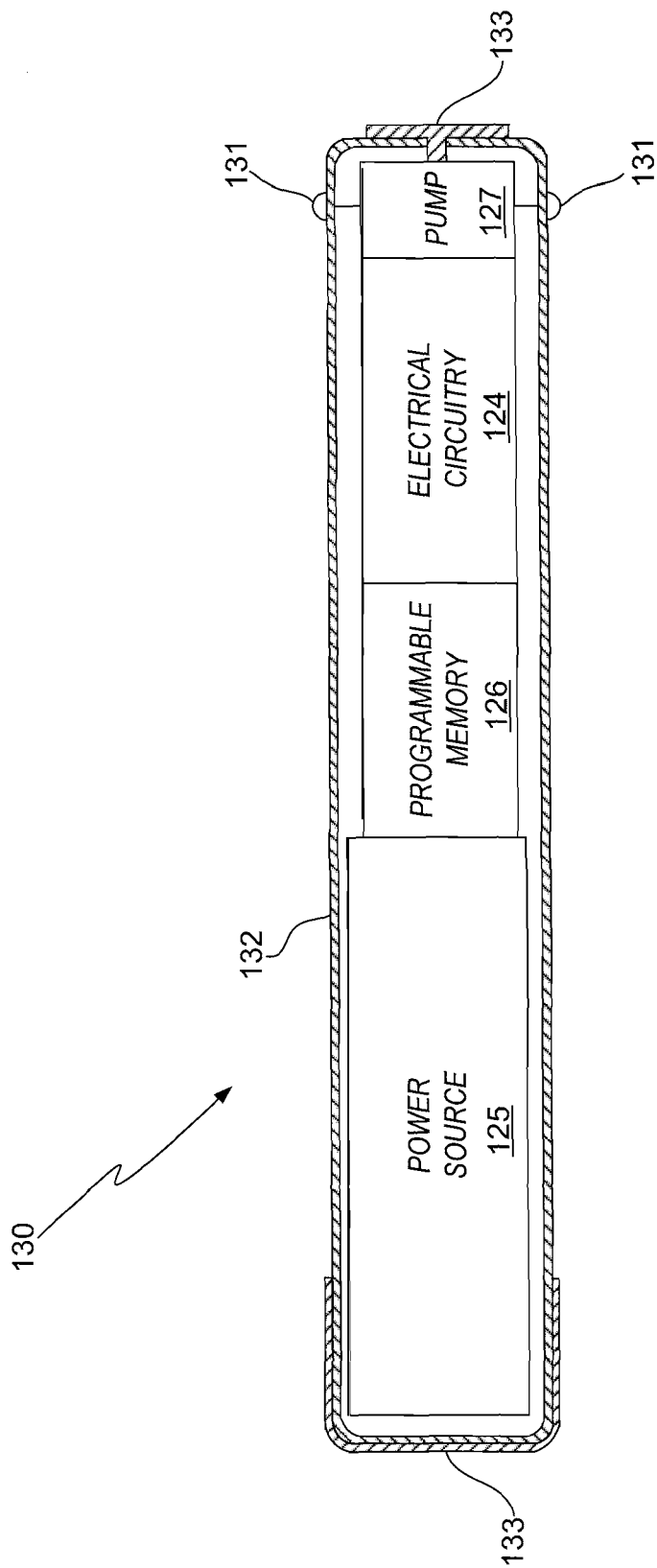
FIG. 3 illustrates an exemplary microstimulator according to principles described herein.

FIG. 3 illustrates an exemplary microstimulator 130 that may be used as the stimulator 120 described herein. Other configurations of the microstimulator 130 are possible, as shown in the above-referenced patents and as described further below.

As shown in FIG. 3, the microstimulator 130 may include the power source 125, the programmable memory 126, the electrical circuitry 124, and the pump 127 described in connection with FIG. 2. These components are housed within a capsule 132. The capsule 132 may be a thin, elongated cylinder or any other shape as best serves a particular application. The shape of the capsule 132 may be determined by the structure of the desired stimulation site and the method of implantation. In some examples, the microstimulator 130 may include two or more leadless electrodes 133 disposed on the outer surface thereof.

The external surfaces of the microstimulator 130 may advantageously be composed of biocompatible materials. For example, the capsule 132 may be made of glass, ceramic, metal, or any other material that provides a hermetic package that will exclude water vapor but permit passage of electromagnetic fields used to transmit data and/or power. The electrodes 133 may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator 130 may also include one or more infusion outlets 131 configured to dispense one or more drugs directly at a stimulation site. Alternatively, one or more catheters may be coupled to the infusion outlets 131 to deliver the drug therapy to a treatment site some distance from the body of the microstimulator 130.

Figure 4A:
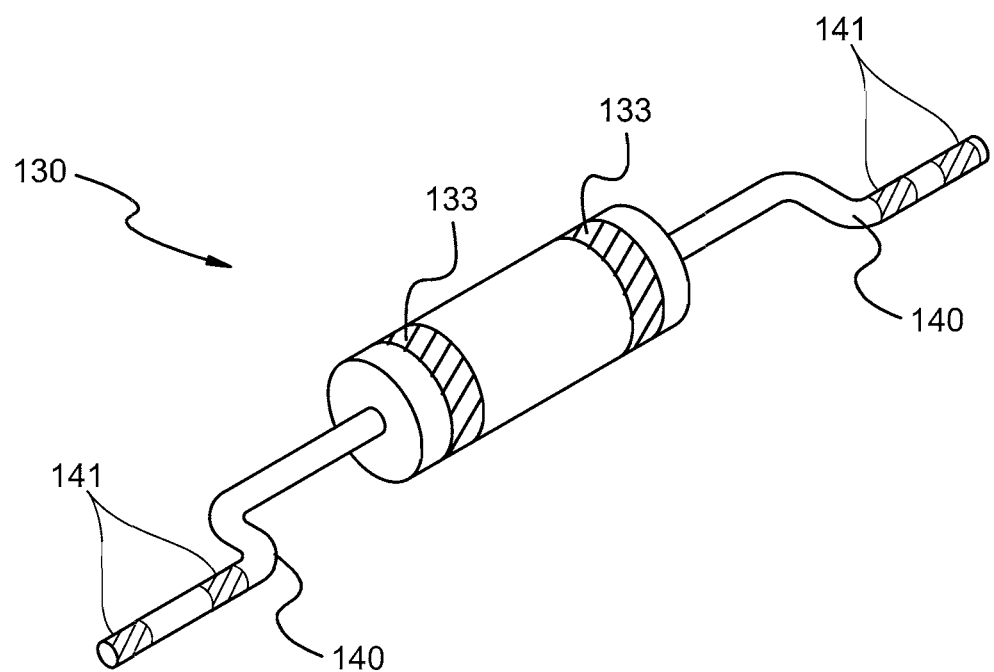
FIG. 4A shows an example of a microstimulator with one or more leads coupled thereto according to principles described herein.
Figure 4C:
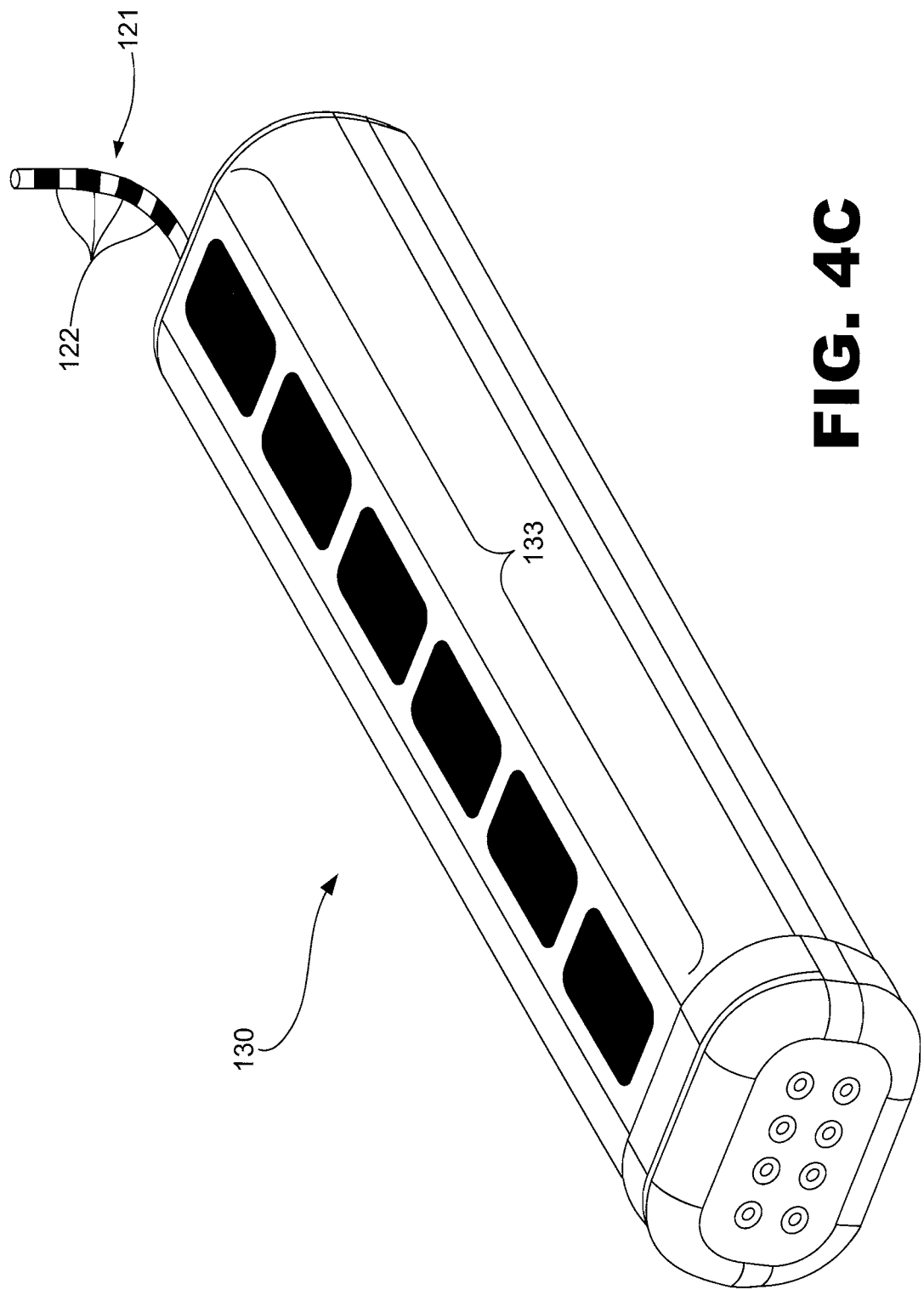
FIG. 4C shows the exemplary microstimulator of FIG. 4B coupled to a lead having a number of electrodes disposed thereon according to principles described herein.

FIGS. 4A-4C show alternative configurations of a microstimulator 130. It will be recognized that the alternative configurations shown in FIGS. 4A-4C are merely illustrative of the many possible configurations of a microstimulator 130. For example, FIG. 4A shows an example of a microstimulator 130 with one or more leads 140 coupled thereto. As shown in FIG. 4A, each of the leads 140 may include one or more electrodes 141 disposed thereon. The microstimulator 130 of FIG. 4A may additionally or alternatively include one or more leadless electrodes 133 disposed on the outer surface thereof.

FIG. 4B illustrates an exemplary microstimulator 130 with a plurality of electrodes 133 disposed on an outer surface thereof. In some examples, any number of electrodes 133 may be disposed on the outer surface of the microstimulator 130. In some alternative examples, as shown in FIG. 4C, the microstimulator 130 may be coupled to a lead 121 having a number of electrodes 122 disposed thereon. Each of the electrodes 133 and 122 may be selectively configured to serve as an anode or as a cathode.

In some examples, the stimulator 120 of FIG. 2 may be communicatively coupled to one or more wireless electrodes disposed at a stimulation site. For example, the stimulator 120 may be configured to wirelessly transmit signals representative of electrical stimulation to one or more stent electrodes or other types of electrodes. Exemplary stent electrodes that may be used in accordance with the systems and methods described herein are described in U.S. Patent Application Publication No. 20070150009, which application is incorporated herein by reference in its entirety. In an embodiment, the stent body is configured as a loop antenna to inductively receive power and communication from a transmit antenna located within or outside the patient.

Figure 5:
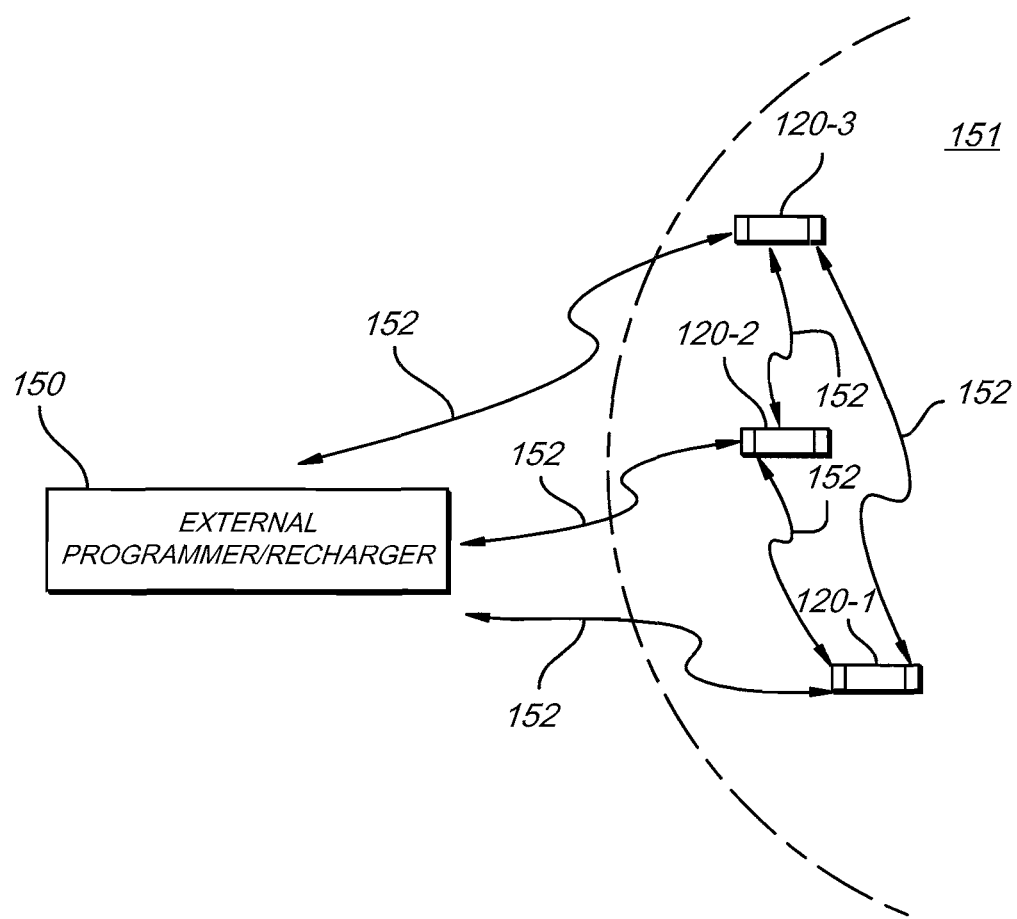
FIG. 5 depicts a number of stimulators configured to communicate with each other and/or with one or more external devices according to principles described herein.

In some examples, the stimulator 120 of FIG. 2 may be configured to operate independently. Alternatively, as shown in FIG. 5, the stimulator 120 may be configured to operate in a coordinated manner with one or more additional stimulators, other implanted devices, or other devices external to the patient's body. FIG. 5 illustrates an exemplary configuration wherein a first stimulator 120-1 implanted within the patient 151 provides a stimulus to a first location, a second stimulator 120-2 provides a stimulus to a second location, and a third stimulator 120-3 provides a stimulus to a third location. In some examples, one or more external devices 150 may be configured to control the operation of each of the implanted devices 120. In some embodiments, an implanted device, e.g., stimulator 120-1, may control, or operate under the control of, another implanted device(s), e.g., stimulator 120-2 and/or stimulator 120-3. Control lines 152 have been drawn in FIG. 5 to illustrate that the external device 150 may communicate or provide power to any of the implanted devices 120 and that each of the various implanted devices 120 may communicate with and, in some instances, control any of the other implanted devices.

As a further example of multiple stimulators 120 operating in a coordinated manner, the first and second stimulators 120-1 and 120-2 of FIG. 5 may be configured to sense various indicators of the need for the sphincter of Oddi to dilate or contract and transmit the measured information to the third stimulator 120-3. The third stimulator 120-3 may then use the measured information to adjust its stimulation parameters and apply stimulation to a stimulation site accordingly. The various implanted stimulators may, in any combination, sense indicators and/or causes of pancreatitis pain due to sphincter of Oddi dysfunction, communicate or receive data regarding such indicators, and adjust stimulation parameters accordingly.

In order to determine the strength and/or duration of electrical stimulation and/or amount and/or type(s) of stimulating drug(s) required to most effectively control sphincter of Oddi function in order to treat pancreatitis pain, various indicators of pancreatitis pain, sphincter of Oddi dysfunction, the need for pancreatic secretion (e.g., to digest food), and/or a patient's response to treatment may be sensed or measured. The stimulator 120 may then adjust the stimulation parameters (e.g., in a closed loop manner) in response to one or more of the sensed indicators. Exemplary indicators include, but are not limited to, neurotransmitter levels, patient input, changes in hormone concentration, detected stomach activity, circumference changes in the duodenum (e.g., as a result of peristalsis), pyloric sphincter contraction, detected food passing through the gastrointestinal tract, a change in one or more pH levels, audible sounds from the stomach (i.e., borborygmus), detected contraction or relaxation of sphincter of Oddi muscles, detected contraction of exocrine tissue around ductal occlusions, and pressure or circumference changes in the bile duct, pancreatic duct, ampulla, and/or duodenum. In some examples, the stimulator 120 may be configured to perform one or more of the measurements. Alternatively, other sensing devices may be configured to perform the measurements and transmit the measured values to the stimulator 120.

Examples of sensing devices that may be used as components of or in conjunction with the stimulator 120 include, but are not limited to, subcutaneous buttons (pressed by the user or a practitioner), hormonal or chemical sensors, piezoelectric sensors, strain gauges, optical sensors, pH detectors, auditory sensors, pressure sensors, and/or combinations thereof.

Thus, one or more external devices may be provided to interact with the stimulator 120, and may be used to accomplish at least one or more of the following functions:

Function 1: If necessary, transmit electrical power to the stimulator 120 in order to power the stimulator 120 and/or recharge the power source 125.

Function 2: Transmit data to the stimulator 120 in order to change the stimulation parameters used by the stimulator 120.

Function 3: Receive data indicating the state of the stimulator 120 (e.g., battery level, drug level, stimulation parameters, etc.).

Additional functions may include adjusting the stimulation parameters based on information sensed by the stimulator 120 or by other sensing devices.

By way of example, an exemplary method of treating pancreatitis pain due to sphincter of Oddi dysfunction may be carried out according to the following sequence of procedures. The steps listed below may be modified, reordered, and/or added to as best serves a particular application.

1. A stimulator 120 is implanted so that its electrodes 122 and/or infusion outlet 129 are in communication with a stimulation site within a patient. As used herein and in the appended claims, the term "in communication with" refers to the stimulator 120, stimulating electrodes 122, and/or infusion outlet 129 being adjacent to, in the general vicinity of, in close proximity to, directly next to, or directly on the stimulation site.

2. One or more stimulation parameters are configured to control sphincter of Oddi function in order to treat pancreatitis pain.

3. The stimulator 120 is programmed with the one or more stimulation parameters configured to control sphincter of Oddi function. The stimulator 120 may then generate and apply at least one stimulus to the stimulation site in accordance with the stimulation parameters. The stimulus may include electrical stimulation, drug stimulation, gene infusion, chemical stimulation, thermal stimulation, electromagnetic stimulation, mechanical stimulation, and/or any other suitable stimulation.

4. When the patient desires to invoke stimulation, the patient sends a command to the stimulator 120 (e.g., via a remote control) such that the stimulator 120 delivers the prescribed stimulation to the stimulation site. For example, the stimulation may be activated by the patient when a particular incident of pancreatitis pain is detected. The stimulator 120 may alternatively or additionally be configured to apply the stimulation to the stimulation site in accordance with one or more pre-determined stimulation parameters and/or automatically apply the stimulation in response to sensed indicators of sphincter of Oddi dysfunction and/or pancreatitis pain.

5. To cease stimulation, the patient may turn off the stimulator 120 (e.g., via a remote control).

6. Periodically, the power source 125 of the stimulator 120 is recharged, if necessary, in accordance with Function 1 described above.

In other examples, the treatment administered by the stimulator 120, i.e., drug therapy and/or electrical stimulation, may be automatic and not controlled or invoked by the patient. It will be recognized that the particular stimulation methods and parameters may vary as best serves a particular application.

Figure 6:
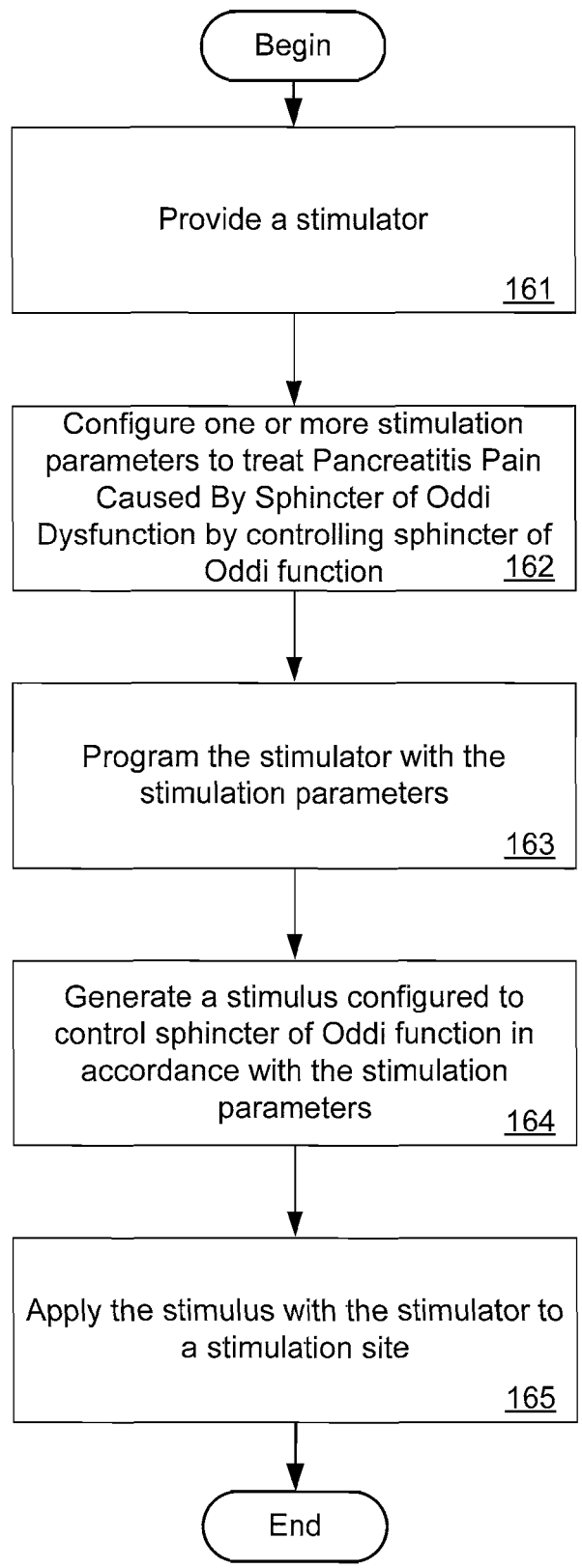
FIG. 6 is a flowchart of an exemplary method of treating pancreatitis pain caused by sphincter of Oddi dysfunction according to principles described herein.

FIG. 6 shows a flowchart of an exemplary method of treating pancreatitis pain caused by sphincter of Oddi dysfunction, according to the principles that have been described in more detail above. While FIG. 6 illustrates exemplary steps according to one embodiment, other embodiments may omit, add to, reorder, and/or modify any of the steps shown in FIG. 6.

In step 161, a stimulator is provided. In step 162, one or more stimulation parameters are configured to treat pancreatitis pain by controlling sphincter of Oddi dysfunction. In step 163, the stimulator is programmed with the stimulator parameters. In step 164, a stimulus configured to control sphincter of Oddi function in accordance with the stimulation parameters is generated. In step 165, the stimulus is applied with the stimulator to a stimulation site. The stimulation site may include any of the stimulation sites described herein.

The stimulator 120 may be implanted within a patient using any suitable surgical procedure such as, but not limited to, small incision, open placement, laparoscopy, or endoscopy. Exemplary methods of implanting a microstimulator, for example, are described in U.S. Pat. Nos. 7,193,539; 5,193, 540; 5,312,439; 6,185,452; 6,164,284; 6,208,894; and 6,051, 017. Exemplary methods of implanting an SCS, for example, are described in U.S. Pat. Nos. 7,501,703; 6,487,446; and 6,516,227. Exemplary methods of implanting a deep brain stimulator, for example, are described in U.S. Pat. Nos. 7,938, 688; 6,016,449; and 6,539,263. All of these listed patents are incorporated herein by reference in their respective entireties.

Figure 7A:
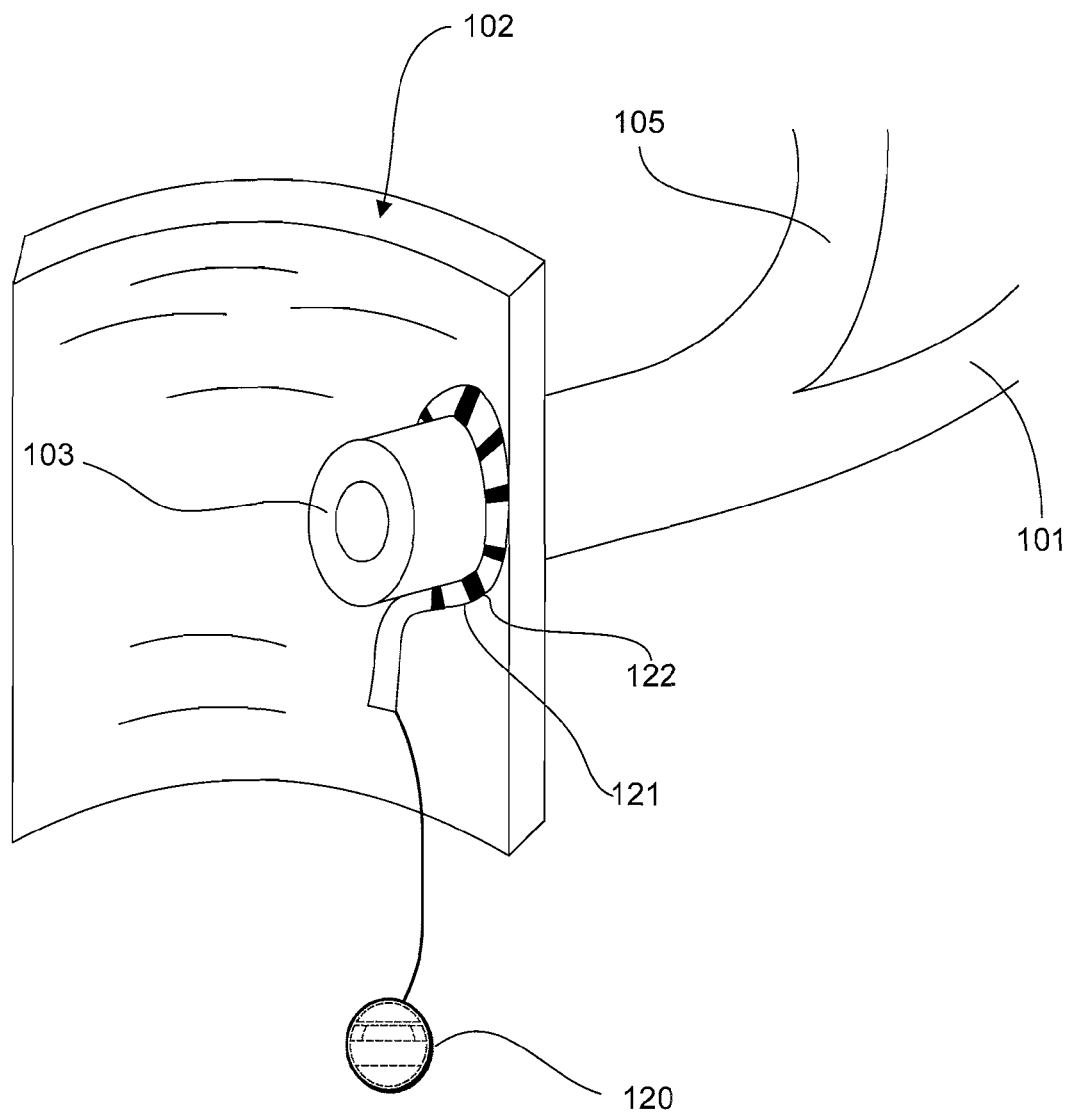
FIGS. 7A-7C illustrate exemplary configurations wherein one or more electrodes coupled to an implantable stimulator have been implanted such that they are in communication with one or more stimulation sites within a patient according to principles described herein.
Figure 7B:
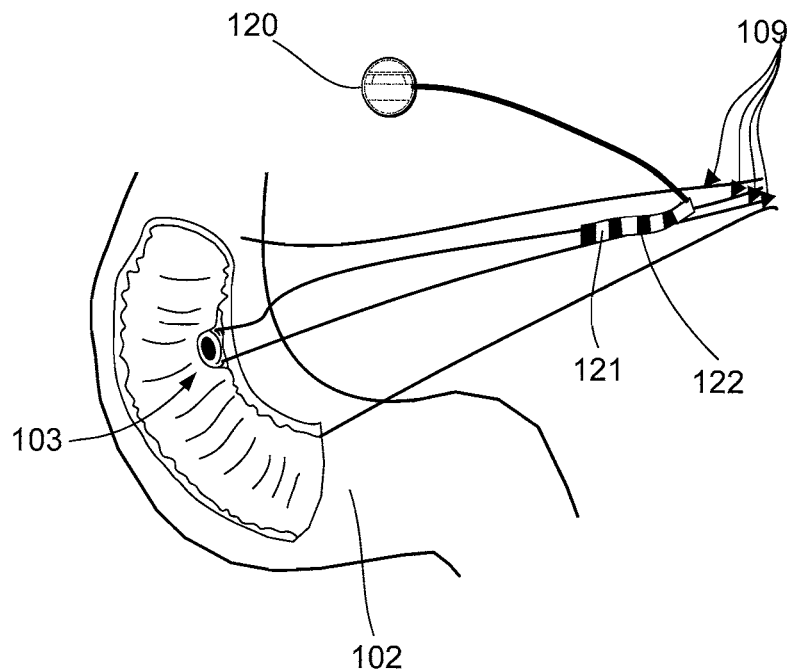
Figure 7C:
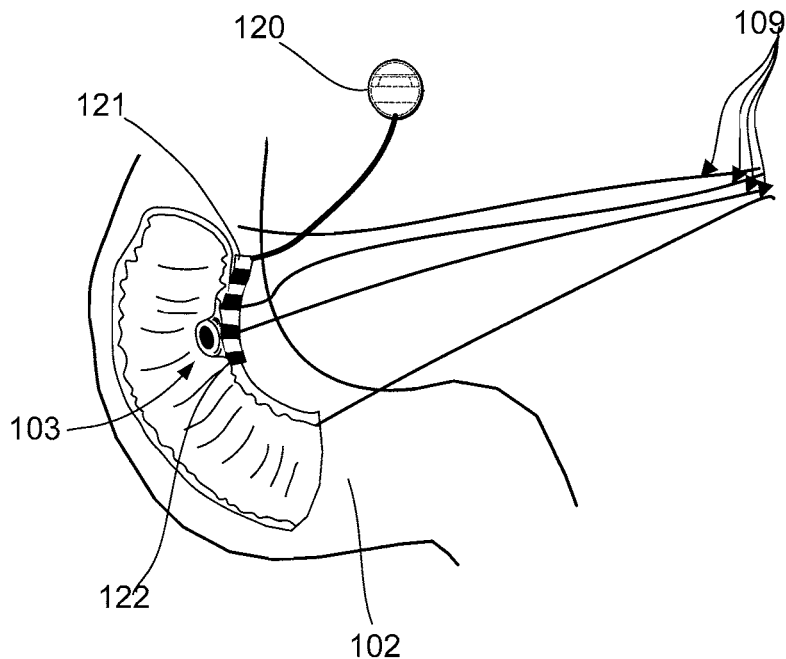

To illustrate, FIGS. 7A-7C illustrate exemplary configurations wherein one or more electrodes 122 coupled to an implantable stimulator 120 have been implanted such that they are in communication with one or more stimulation sites within a patient. The configurations shown in FIGS. 7A-7C are merely illustrative of the many different implant configurations that may be used in accordance with the systems and methods described herein.

In the example of FIG. 7A, the distal portion of a lead 121 having electrodes 122 disposed thereon may be placed around at least a portion of the sphincter of Oddi 103 such that the electrodes 122 are in communication with one or more of the regions of muscle tissue of the sphincter of Oddi 103. Additionally or alternatively, the lead 121 may be implanted such that the electrodes 122 are in communication with one or more of the nerves that innervate the sphincter of Oddi. It will be recognized that although only an electrode lead 121 is shown in FIG. 7A, a catheter 123 may additionally or alternatively be implanted for drug stimulation in a similar manner.

As shown in FIG. 7A, the lead 121 may be coupled to a stimulator 120 that has been implanted in a more convenient location. For example, the stimulator 120 may be subcutaneously implanted within the abdomen. This may allow easy access to the stimulator 120 and maximize the efficiency of power recharging and/or data communication operations between the stimulator 120 and an external instrument. In some alternative examples, an appropriately sized stimulator 120 with one or more electrodes 122 disposed thereon may be implanted at least partially within the wall of the duodenum 102.

FIG. 7B shows an electrode lead 121 disposed at or near one of the pre-ganglionic cholinergic nerves 109 that innervates the sphincter of Oddi 103. FIG. 7C shows an electrode lead 121 placed at a nerve ending of one of the pre-ganglionic cholinergic nerves 109. As shown in both FIGS. 7B and 7C, the electrode leads 121 may be coupled to stimulators 120 located in more surgically convenient locations. It will be understood that the lead 121 and/or stimulator 120 may be implanted at any other suitable stimulation site as may serve a particular application.

Figure 8:
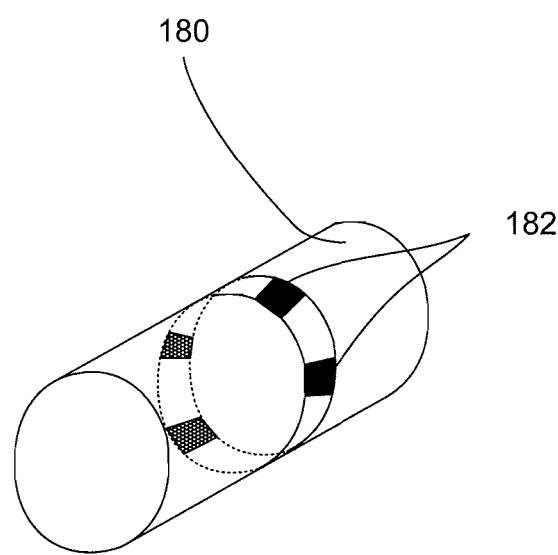
FIG. 8 illustrates an exemplary configuration wherein one or more electrodes are disposed on a stent according to principles described herein.

FIG. 8 shows an exemplary stent 180 that may be implanted within a patient in accordance with the systems and methods described herein. The stent may include one or more stent electrodes 182 disposed thereon through which electrical stimulation may be applied to one or more stimulation sites within the patient. In some examples, the stent 180 may be implanted within the sphincter of Oddi 103 or within the confluence of the common bile duct 181 and the pancreatic duct 101. The stent 180 may additionally or alternatively be implanted in any other suitable location within the patient.

Figure 9:
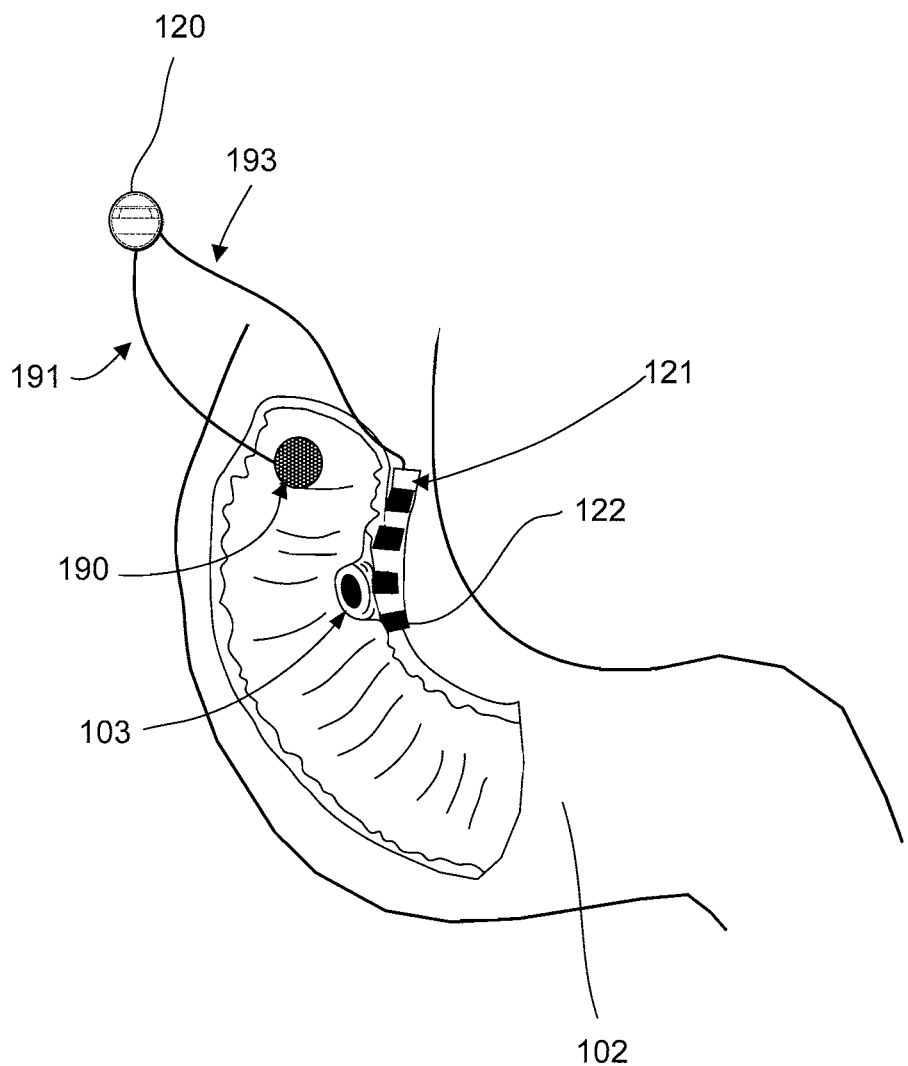
FIG. 9 illustrates an exemplary configuration wherein an implanted stimulator is in communication with an implanted sensing device according to principles described herein.

FIG. 9 illustrates an exemplary configuration wherein a sensing device 190 may be implanted within the patient and communicatively coupled to the stimulator 120. As shown in FIG. 9, a lead 121 having electrodes 122 may be disposed at a stimulation site within the patient (e.g., along a surface of the duodenum 102 near the sphincter of Oddi 103). The sensing device 190 may be coupled to the duodenum 102, for example, or to any other tissue within the patient. The lead 121 and sensing device 190 may be in electrical communication with the stimulator 120 through connections 191 and 193. The stimulator 120 may include electrical circuitry configured to interpret biological parameters detected by the sensing device 190 to determine optimal stimulation parameters.

The sensing device 190 shown in FIG. 9 may include any type of sensing device described herein. For example, the sensing device 190 may include a strain gauge or piezoelectric element configured to measure changes in the circumference of the duodenum 102.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a patient with pancreatitis pain, comprising:
   generating a first stimulus and a second stimulus with a stimulator implanted within the patient; and
   applying the first stimulus and the second stimulus to a stimulation site comprising at least one or more of a region of the sphincter of Oddi and a nerve innervating a sphincter of Oddi of the patient, such that the first applied stimulus contracts the sphincter of the Oddi during a first period and the second applied stimulus relaxes the sphincter of the Oddi during a second period to treat the pancreatitis pain.

2. The method of claim 1, wherein the stimulation site comprises at least one or more of a sphincter of Oddi muscle tissue, a nerve innervating the sphincter of Oddi muscle tissue, a pre-ganglionic cholinergic nerve, an efferent nerve, a tissue of the duodenum near the sphincter of Oddi, and a pancreatic duct.

3. The method of claim 1, wherein the first stimulus and the second stimulus performs at least one of a blocking and an invoking of one or more myoelectrical potentials at the stimulation site.

4. The method of claim 1, wherein the stimulator is coupled to one or more electrodes, and wherein at least one of the first stimulus and the second stimulus comprises a stimulation current delivered via the electrodes.

5. The method of claim 1, wherein at least one of the first stimulus and the second stimulus comprises an infusion of one or more drugs at the stimulation site.

6. The method of claim 1, further comprising:
   configuring one or more stimulation parameters designed to control the function of the sphincter of Oddi; and
   programming the stimulator with the one or more stimulation parameters.

7. The method of claim 6, further comprising sensing at least one indicator related to the pancreatitis pain and using the at least one sensed indicator to adjust one or more of the stimulation parameters.

8. The method of claim 7, wherein the indicator comprises at least one or more of a contraction of one or more muscles of the sphincter of Oddi, a relaxation of one or more muscles of the sphincter of Oddi, a need for pancreatic secretion, a neurotransmitter level, a patient input, a change in hormone concentration, a detected stomach activity, a circumference change in a duodenum, a pyloric sphincter contraction, a detection of food passing through the gastrointestinal tract, a change in pH, an audible sound, a contraction of exocrine tissue, a pressure change in a bile duct, a change in myoelectrical potentials, a pressure change in a pancreatic duct, a pressure change in an ampulla, a pressure change in the duodenum, a circumference change in the pancreatic duct, a circumference change in the ampulla, and a circumference change in the duodenum.

9. The method of claim 7, further comprising sensing the at least one indicator with at least one or more of a patient feedback sensor, a hormonal sensor, a chemical sensor, a piezoelectric sensor, a strain gauge, an optical sensor, a pH sensor, an auditory sensor, and a pressure sensor.

10. The method of claim 1, further comprising implanting the stimulator within the patient.

11. The method of claim 1, wherein the first period is when gastrointestinal activity is relatively low, and wherein the second period is when gastrointestinal activity is relatively high.

12. The method of claim 1, wherein the first stimulus is applied to the stimulation site between meals, and wherein the second stimulus is applied to the stimulation site during meals.

13. The method of claim 1, wherein the stimulation site comprises the sphincter of Oddi of the patient.

14. The method of claim 1, wherein the stimulation site comprises the nerve innervating the sphincter of Oddi of the patient.

* * * * *